(12) United States Patent
Fleury

(10) Patent No.: US 6,695,515 B1
(45) Date of Patent: Feb. 24, 2004

(54) DISPOSABLE MULTI-COMPARTMENT APPLICATOR

(75) Inventor: Lydie Fleury, Puiseux (FR)

(73) Assignees: Verpackungs Service GmbH, Weingarten (DE); Tir Groupe, Puteaux (FR); Alydie Fleury, Puiseux en France (FR)

( * ) Notice: Subject to any disclaimer, the term of this patent is extended or adjusted under 35 U.S.C. 154(b) by 0 days.

(21) Appl. No.: 09/743,217

(22) PCT Filed: Jul. 8, 1998

(86) PCT No.: PCT/FR98/01463

§ 371 (c)(1),
(2), (4) Date: Jan. 17, 2001

(87) PCT Pub. No.: WO00/02513

PCT Pub. Date: Jan. 20, 2000

(51) Int. Cl.⁷ .......................... B65D 35/22; A45D 34/00
(52) U.S. Cl. ........................ 401/132; 401/133; 401/196
(58) Field of Search ............... 602/41, 42, 43, 602/48, 58; 424/402, 401; 401/132, 133, 196

(56) References Cited

U.S. PATENT DOCUMENTS

| | | | |
|---|---|---|---|
| 2,377,177 A | | 5/1945 | Pfleumer |
| 3,635,567 A | * | 1/1972 | Richardson, Jr. ........... 401/132 |
| 3,826,259 A | | 7/1974 | Bailey |
| 4,812,067 A | * | 3/1989 | Brown et al. ............... 401/132 |
| 5,558,874 A | * | 9/1996 | Haber et al. ............... 424/402 |
| 5,681,574 A | * | 10/1997 | Haber et al. ............... 424/402 |

FOREIGN PATENT DOCUMENTS

| | | | | |
|---|---|---|---|---|
| AU | 702273 | * | 10/1996 | ........... A61F/15/00 |
| DE | 1 087 758 | | 8/1960 | |
| EP | 0 737 463 | | 10/1996 | |
| FR | 1 111 282 | | 2/1956 | |
| FR | 1 292 852 | | 5/1962 | |
| FR | 2 255 224 | | 7/1975 | |

* cited by examiner

Primary Examiner—Danton D. DeMille
Assistant Examiner—Quang D Thanh
(74) Attorney, Agent, or Firm—Foley & Lardner

(57) ABSTRACT

A disposable multi-compartment applicator has two receptacle blisters hermetically closed by a film. One of the receptacle blisters may contain a liquid, fluid, cream, or paste element and the other receptacle blister may contain a dry element, pad, compress, or a material having absorption and restitution power. Squeezing one receptacle blister separates part of the film along a zone of weakness to put the liquid element in communication with the dry element, while keeping the device completely hermetic. After the dry element has been in communication with the liquid element, the dry element may be uncovered for first-aid or other use. The applicator may additionally house sticking plaster or a bandage for covering a wound that has been cleaned using the applicator.

6 Claims, 5 Drawing Sheets

DISPOSABLE MULTI-COMPARTMENT APPLICATOR

BACKGROUND OF THE INVENTION

This single-use and disposable throw-away device contains care items of a medical nature and it guarantees total and long-lasting non-contamination and sterility of the various packaged and assembled elements. This example is not in any way limiting as to the substances, components, or materials employed and assembled together, or as to the dimensions and shapes shown.

Its use and application of novel character compared with prior assemblies forming kits that are peelable, cuttable, or extractable, are confirmed by its operating principles of squeezing, bursting, and uncovering. These three principles enable the device to be used and applied without ever separating the contained elements from the container element, thereby guaranteeing perfect sterility for the assembly and non-contamination of the elements for application both before and during use. Furthermore, given that none of the elements can be lost or separated from the assembly, this provides protection for the environment.

SUMMARY OF THE INVENTION

This invention is described in an application to care of a medical nature, but it can be applied in like manner in the fields of cosmetics, foodstuffs, cleaning, various kinds of maintenance, etc.

The elements making up the assembly of the device are suitable as a function of the intended field of its application.

This invention provides a device combining a plurality of elements and substances that are packaged and assembled together in a manner that is completely hermetic and without risk for the user regardless of the field, conditions of application, age of user, and user knowledge in said field.

At no time at, before, or during application does the user come into contact with any of these substances (liquid, cream, paste, applicator pads, protective sticking-plasters, in this example applied to the field of body hygiene and care, but also in other fields of application).

Three elements are associated indissociably so as to constitute a single element for an application.

Completely hermetic, sterile, and non-contaminatable because the container is a single piece and it is not made up from separate pieces fitted together.

Liquid and solid elements are put into communication merely by squeezing, without using a distribution channel that might be prevented from operating by an obstruction.

All of the elements of the device are held together before, during, and after use because of the one-piece structure of the device having no elements that are extractable or peelable, thereby guaranteeing that the device is sterile before and during use and also protecting the environment by eliminating any risk of one of the elements of the device becoming lost.

Given the resulting simplified design, implementation on an industrial scale providing full guarantees of safety and sterility puts the device within financial reach of all users whatever their age or their degree of competence in the field of application.

A single-use and disposable first-aid device representing a one-piece assembly is characterized by its simplicity of use, the guarantee of non-contamination before and during use, and the lack of risk of contamination and soiling of the user or by the user, and it is made up of a thermoformed element having two blisters acting as receptacles, respectively for the fluid element and for the dry element, which elements are protected from any contamination by heat sealing using aluminum, plastic, or any other material used in industry to guarantee a completely hermetic seal.

The liquid element is put into communication with the dry element merely by squeezing the liquid receptacle, thereby always breaking part of the heat sealing and causing the dry element to be soaked while guaranteeing that the assembly is completely hermetic.

Another important element of invention, characterized by the disposition of a compartment (or pocket) in indissociable manner on the heat sealing causing the device as a whole to form an integral single piece, which compartment in the present example contains a protective sticking-plaster for covering a wound after it has been disinfected, the sticking-plaster being taken hold of not by peeling away the compartment but by tearing away the center of the compartment, thus providing the advantage of ensuring that no contact is made with the sticking-plaster when it is taken hold of and applied.

BRIEF DESCRIPTION OF THE DRAWINGS

These and other features, aspects and advantages of the present invention will become apparent from the following description, appended claims, and the accompanying exemplary embodiments shown in the drawings, which are briefly described below.

DETAILED DESCRIPTION

Figure 1:
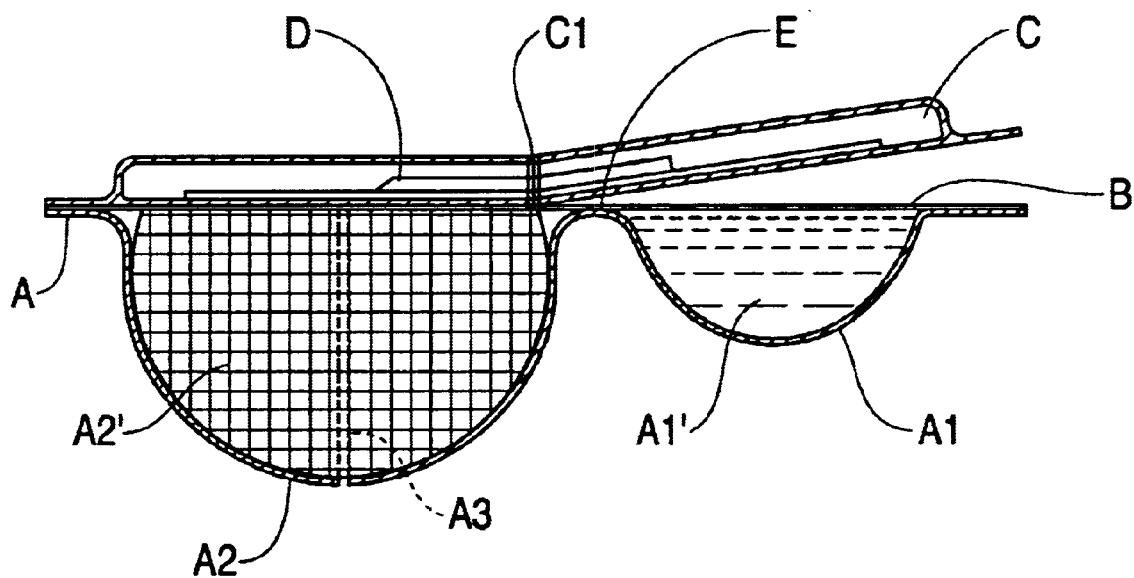
FIG. 1 is a cross sectional view of a disposable multiple compartment applicator in accordance with one embodiment of the present invention.
Figure 2:
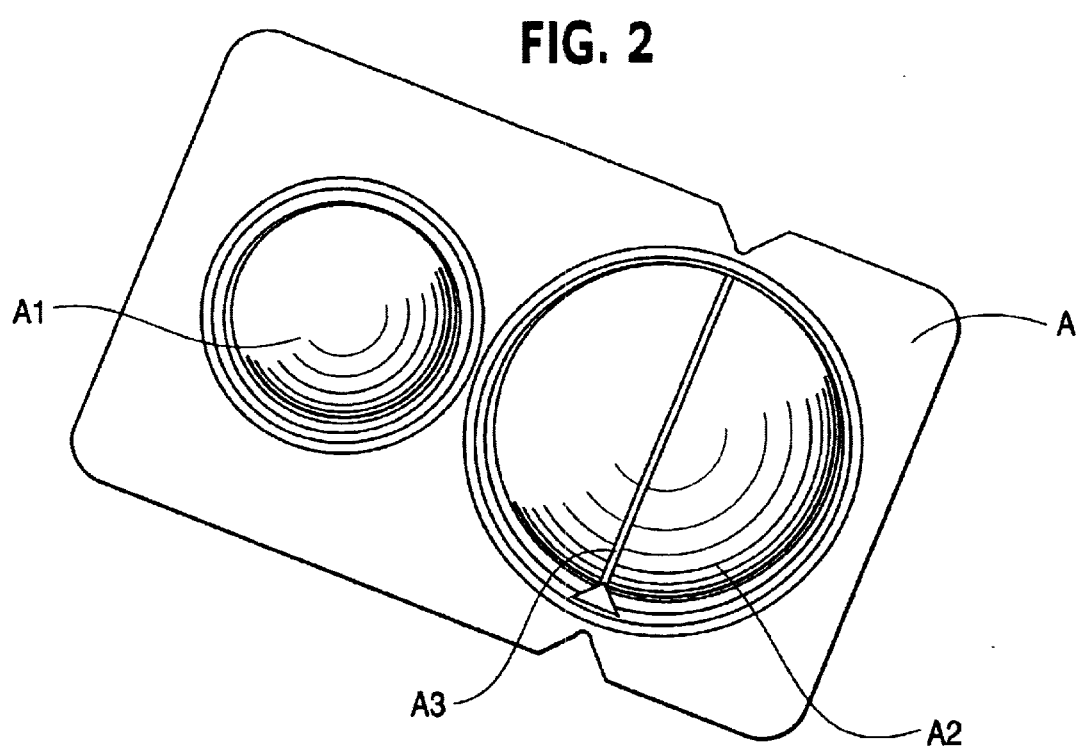
FIG. 2 is a bottom view of the applicator of FIG. 1.
Figure 3:
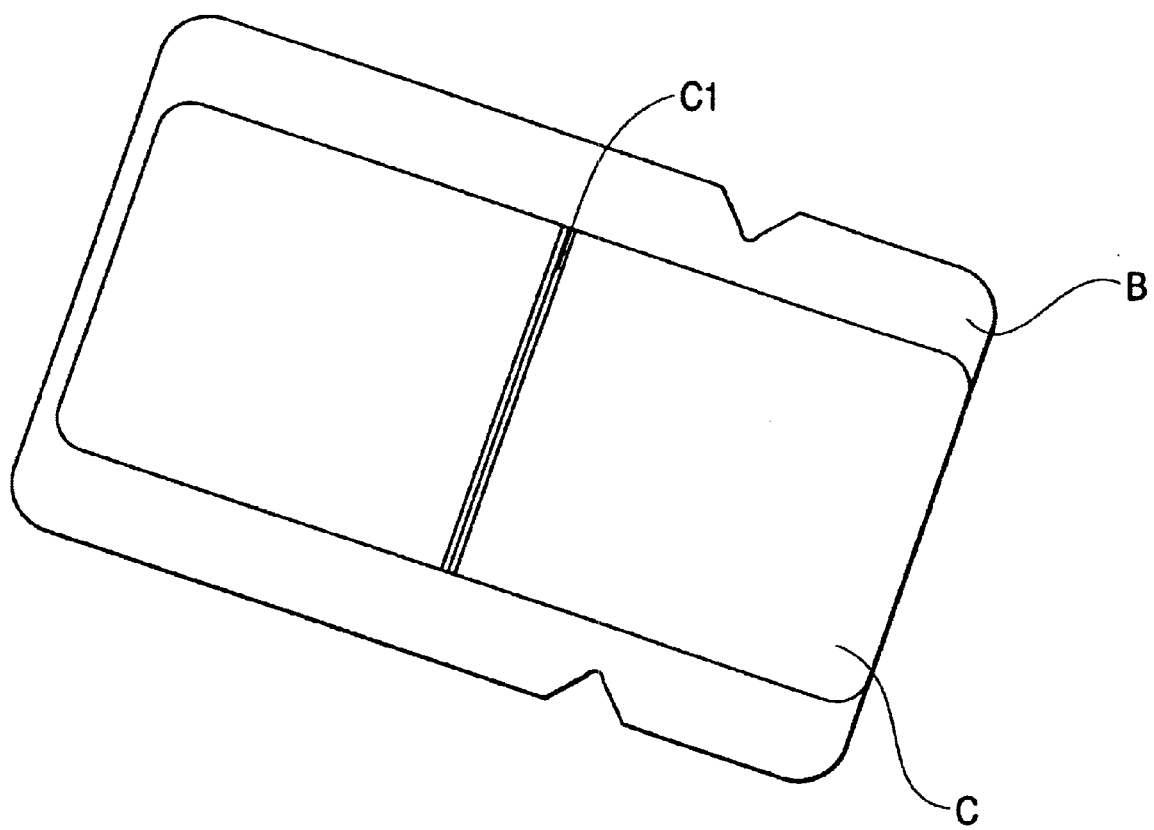
FIG. 3 is a top view of the applicator of FIG. 1.
Figure 4:
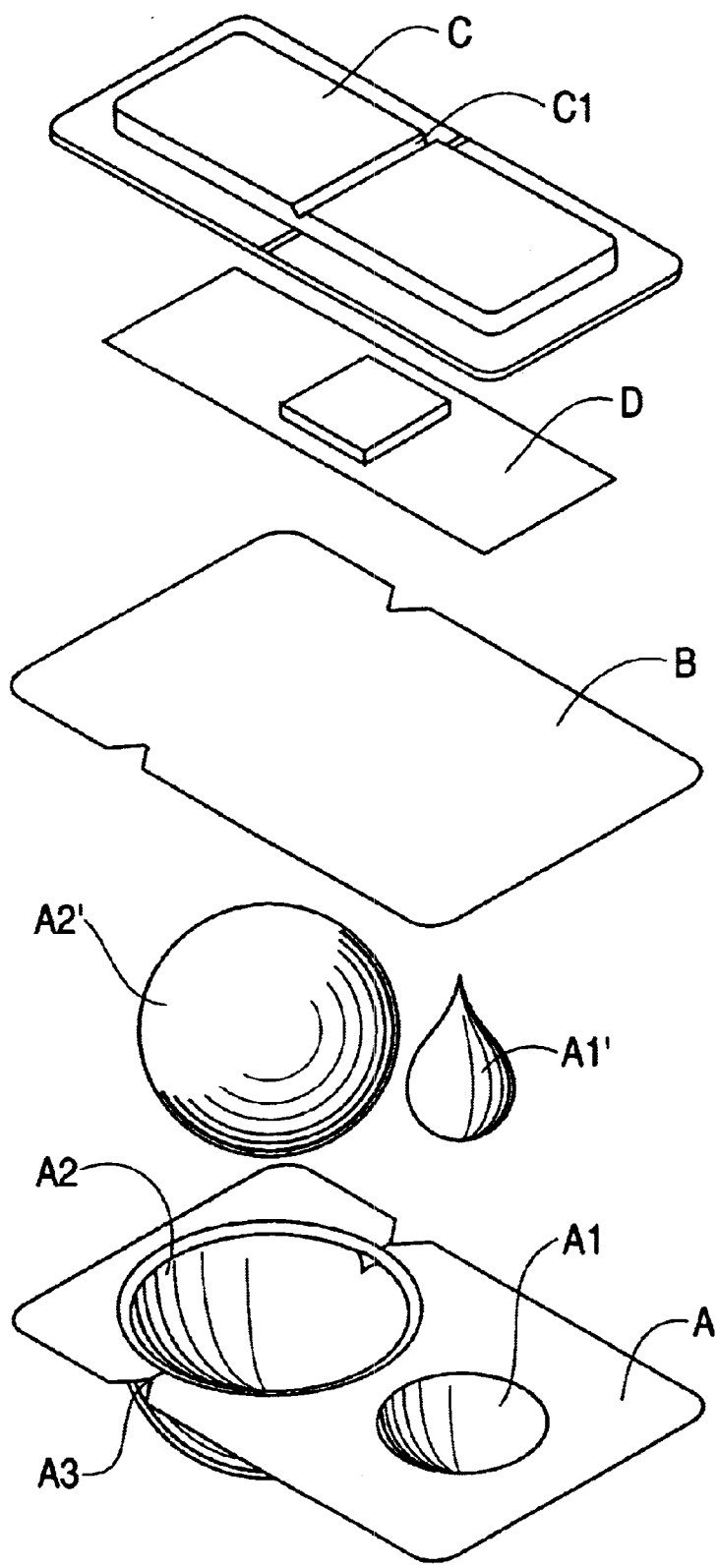
FIG. 4 is an exploded top perspective view of the applicator of FIG. 1.
Figure 5:
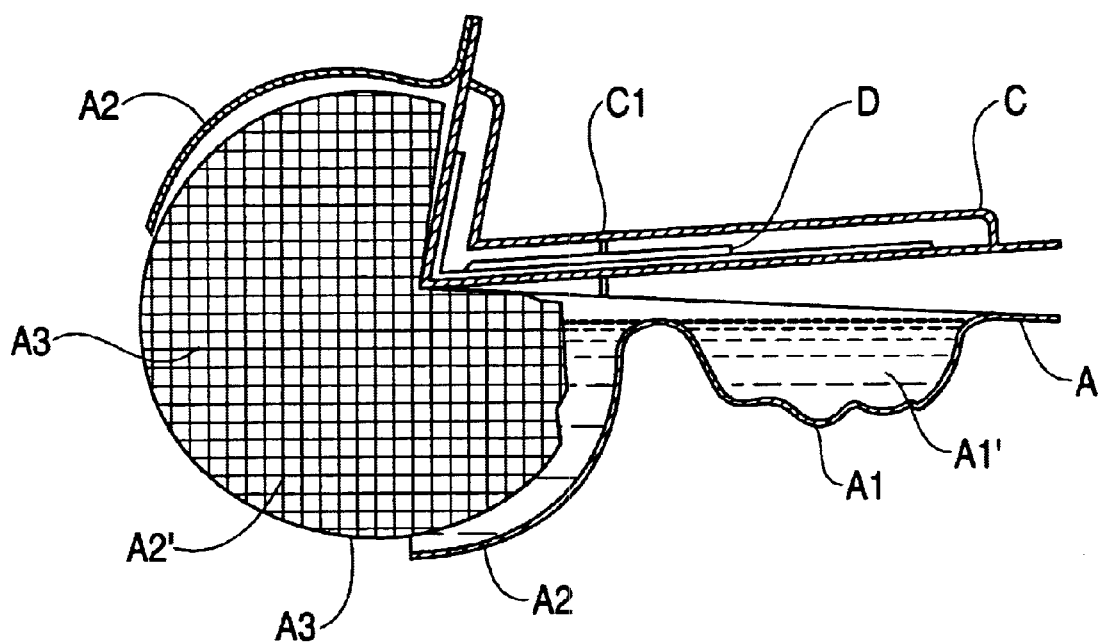
FIG. 5 is a cross sectional view of the applicator of FIG. 1 shown during use.

In one embodiment of the invention, the multi-compartment applicator may be used to care for a body. However, the invention is not limited to this use. Other applications will occur to those skilled in the art.

Illustrated in the drawings which show a thermoformed plate A having two blisters A1 and A2 respectively provided for A1 to package the liquid, cream, or paste element A1', and for A2 to package the dry element A2', had compress or any other synthetic or natural fibber element having absorption and restitution power, the blister A2 being characterized by the fact that it includes a transverse line of weakness A3 enabling that the dry element to be uncovered after it has been soaked for application purposes.

The dry and liquid elements are retained in their respective blisters in a manner that is completely hermetic and sterile by a heatsealable film B covering in indissociable manner the opposite faces of the blisters receiving the liquid and dry elements.

The film B is itself provided with a pocket C that can be torn at its center C1 and that contains a sticking-plaster D for protecting the skin, in this example.

Use of the Device

Merely squeezing the blister A1 containing the fluid element A1' has the effect of separating the heatsealable film B from the plate A at the weakest point, thus allowing the fluid element A1' to communicate with the dry element, said weakest point E being situated between the blisters A1 and A2. Once the applicator A2' has been impregnated, it suffices to fold the blister A2 through 180°, with folding and uncovering of the impregnated applicator being facilitated by the transverse line of weakness A3.

This method has the clear advantages that the impregnated applicator A2' is never touched and of guaranteeing that it is held in the blister A2 during application, the assembly remaining integral and indissociable, thus guaranteeing non-contamination and preserving the environment.

After the fluid, cream, or paste element A1' for disinfecting, drying, or cleaning has been applied by means of the applicator A2' in the form of a compress, pad, or absorbing and restituing element of synthetic or natural fibber or material, the sticking-plaster D for protecting the skin is taken hold off by tearing the center C1 of the pocket C, which has the advantage of handling and applying the sticking-plaster D with the remaining portion of the pocket (C) (or half-pocket C), thereby ensuring that the sticking-plaster for protecting the skin is not touched and contaminated at the moment it is applied.

What is claimed is:

1. A device comprising:
    a first blister housing a first element;
    a second blister housing a second element;
    a film forming at least a first boundary portion of the first blister and forming at least a first boundary portion of the second blister;
    a zone of weakness arranged such that, by squeezing one or both of the blisters, at least a part of the film separates from a container at the zone of weakness to allow the first element to be in communication with the second element; and
    a line of weakness formed integrally within a second boundary portion of one of the blisters, wherein the second boundary portion is not formed by the film, wherein folding the device through an angle of about 180° along the line of weakness causes the second boundary portion to open at the line of weakness without tearing the film, wherein the device includes a dispensing assembly comprising the container and the film, the dispensing assembly being adapted to hermetically contain the first and second elements, and wherein after folding, the dispensing assembly remains together in one piece.

2. A device according to claim 1, wherein the first and second blisters are formed in the container, and wherein the film hermetically closes the first and the second elements with the first and second blisters, respectively.

3. A device according to claim 1, further comprising a pocket disposed over the film, the pocket containing a sticking-plaster.

4. A device according to claim 1, wherein said first element is one of a liquid, cream, or paste.

5. A device according to claim 1, wherein said second element is one of a solid element, compress, pad, natural fiber, or synthetic fiber.

6. A device according to claim 1, wherein:
    said first element is a liquid element;
    said second element is a dry element;
    squeezing One or both of the blisters places the liquid element in communication with the dry element while keeping the device hermetic; and
    after squeezing, folding the device along the line of weakness causes the second boundary portion of the second blister to open at the line of weakness and uncovers the dry element soaked by the liquid element.

* * * * *